(12) United States Patent
Singh

(10) Patent No.: US 11,266,316 B2
(45) Date of Patent: Mar. 8, 2022

(54) SYSTEMS AND METHODS FOR DIURNAL CURVE TRACKING AND ANALYSIS

(71) Applicant: Kinsa Inc., San Francisco, CA (US)

(72) Inventor: Inder Raj Singh, San Francisco, CA (US)

(73) Assignee: Kinsa Inc., San Francisco, CA (US)

( * ) Notice: Subject to any disclaimer, the term of this patent is extended or adjusted under 35 U.S.C. 154(b) by 0 days.

(21) Appl. No.: 17/245,157

(22) Filed: Apr. 30, 2021

(65) Prior Publication Data
US 2021/0345884 A1 Nov. 11, 2021

Related U.S. Application Data

(60) Provisional application No. 63/056,040, filed on Jul. 24, 2020, provisional application No. 63/044,401, filed on Jun. 26, 2020, provisional application No. 63/021,634, filed on May 7, 2020.

(51) Int. Cl.
| | |
|---|---|
| *A61B 5/01* | (2006.01) |
| *A61B 5/00* | (2006.01) |
| *G16H 50/20* | (2018.01) |
| *G16H 40/67* | (2018.01) |
| *G16H 50/30* | (2018.01) |
| *G16H 50/50* | (2018.01) |

(52) U.S. Cl.
CPC .............. *A61B 5/01* (2013.01); *A61B 5/0008* (2013.01); *A61B 5/6801* (2013.01); *A61B 5/6898* (2013.01); *A61B 5/7275* (2013.01); *G16H 40/67* (2018.01); *G16H 50/20* (2018.01); *G16H 50/30* (2018.01); *G16H 50/50* (2018.01); *A61B 2562/0271* (2013.01)

(58) Field of Classification Search
None
See application file for complete search history.

(56) References Cited

U.S. PATENT DOCUMENTS

| | | | |
|---|---|---|---|
| 2006/0178567 A1* | 8/2006 | Goh | G01S 5/0009 600/300 |
| 2007/0161921 A1* | 7/2007 | Rausch | G16H 40/63 600/549 |
| 2010/0042013 A1* | 2/2010 | Cuesta Frau | A61B 5/0008 600/549 |
| 2017/0061074 A1* | 3/2017 | Singh | G16H 40/67 |
| 2017/0367651 A1 | 12/2017 | Tzvieli et al. | |
| 2018/0206730 A1 | 7/2018 | Abreu | |
| 2019/0110692 A1 | 4/2019 | Pardey et al. | |

FOREIGN PATENT DOCUMENTS

WO   2020013830 A1   1/2020

OTHER PUBLICATIONS

Rodriquez, Kari; International Search Report and Written Opinion of the International Searching Authority, issued in International Patent Application No. PCT/US2021/030068; dated Aug. 10, 2021; 11 pages.

* cited by examiner

*Primary Examiner* — Benjamin S Melhus
(74) *Attorney, Agent, or Firm* — Ulmer & Berne LLP

(57) ABSTRACT

Systems and methods for diurnal curve generations, tracking, and analysis are provided. Based on a user's demographic, or a user's baseline diurnal curve, insights into a user's temperature reading can be produced. Such insights can be used to, for example, assess the probability that the user is experiencing a fever, which can be used in screening for medical diagnostic testing.

22 Claims, 13 Drawing Sheets

SYSTEMS AND METHODS FOR DIURNAL CURVE TRACKING AND ANALYSIS

CROSS-REFERENCE TO RELATED APPLICATIONS

This application claims the benefit of U.S. Ser. No. 63/021,634, filed on May 7, 2020, U.S. Ser. No. 63/044,401, filed on Jun. 26, 2020, and U.S. Ser. No. 63/056,040, filed on Jul. 24, 2020, the disclosures of which are each incorporated herein by reference in their entirety.

BACKGROUND

Normal body temperature is considered to be 37° C. (98.6° F.), however, a variation is typically seen over time. Among normal individuals, mean daily temperature can differ by 0.5° C. (0.9° F.), and daily variations can be as much as 0.5° C. to 1.0° C. The nadir in body temperature usually occurs at about 4 a.m. and the peak at about 6 p.m. This circadian rhythm is sometimes referred to as a diurnal temperature curve.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
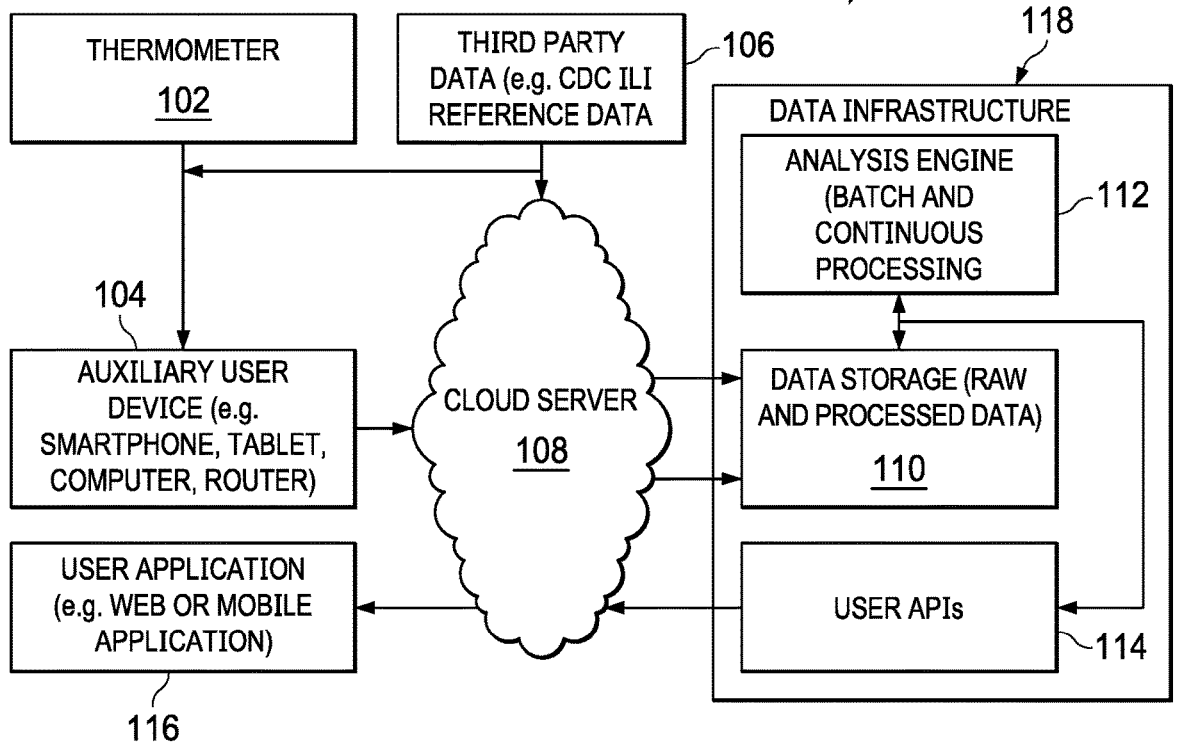
FIG. 1 schematically illustrates an end-to-end illness data collection and processing system in accordance with one non-limiting embodiment.

Various non-limiting embodiments of the present disclosure will now be described to provide an overall understanding of the principles of the structure, function, and use of systems, apparatuses, devices, and methods disclosed. One or more examples of these non-limiting embodiments are illustrated in the selected examples disclosed and described in detail with reference made to FIGS. 1-14 in the accompanying drawings. Those of ordinary skill in the art will understand that systems, apparatuses, devices, and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to the figures. The examples discussed herein are examples only and are provided to assist in the explanation of the apparatuses, devices, systems and methods described herein. None of the features or components shown in the drawings or discussed below should be taken as mandatory for any specific implementation of any of these apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identification of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented, but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

As described in more detail below, the present disclosure generally relates to systems and methods to collect temperature data from people using a temperature sensing probe in communication with a mobile communication device. In accordance with various embodiments, the systems and methods described herein can utilize temperature measurement datasets (e.g., stored or expressed as diurnal curves, temperature timelines, temperature ranges, or other datasets) generated from temperature tracking and analysis to determine whether an individual has an illness. Such an approach can make such determination more accurately and earlier than conventional techniques. For instance, as described in more detail below, illness can be detected prior to the onset of a fever based on characteristics of a temperature dataset (e.g., an unexpected diurnal curve shape, a temperature outside of a particular range for that type of user at that time) that can be present hours before presentation of a fever or other more obvious symptom. Moreover, the age and gender of a user can also be utilized by the presently disclosed embodiments to further assess the user's temperature dataset and determine whether there is a deviation from expected values.

Additionally, because fevers are part of an inflammatory response, they occur with non-infectious conditions including malignancies and autoimmune diseases and are also subject to diurnal patterns. The fact that temperature datasets such as diurnal patterns can be influenced by an inflammatory response has great clinical and public health importance. Because of this diurnal temperature pattern, however, capturing temperature measurements for a temperature dataset at the wrong time of day may decrease the likelihood of detecting a true fever (e.g., a temperature of 98.6° F. may be considered normal if measured at a first point during a 24 hour period, but may indicate an underlying health issue if measured at a second point during a 24 hour period). Understanding how the diurnal temperature patterns and other temperature datasets relate to an individual measurement taken at a particular time can impact the ability to detect true fevers for clinical and public health purposes. In accordance with some embodiments described herein, a model of temperature can be used to, for example, determine the probability of detecting a true fever during a febrile episode across different age groups, depending on the time of day.

The systems and methods described herein can utilize a temperature sensing probe communicatively coupled with one or more mobile computing devices (referred to herein as a "smart health support app," "smart thermometer," or "smart thermometers"). In some embodiments, the temperature sensing probe is an oral, forehead, or ear thermometer that can be used to intermittently measure a user's temperature throughout a period of time. In other embodiments, the temperature sensing probe can be incorporated into a compact wearable computer, sometimes called a "wearable device," such as a smart watch, a fitness tracker, a heart rate monitor, or other type of continual temperature monitoring device. In yet other embodiments, the temperature sensing probe can be incorporated into a device used for continuous patient temperature monitoring in a hospital or clinical setting. In any event, either based on a series of intermittent temperature measurements (i.e., 3+ per day), or based on continual temperature measurement, some systems in accordance with the present disclosure can track and monitor for changes in a user's temperature dataset or diurnal curve. As described in more detail below, based on characteristics or changes exhibited by the user's diurnal curve pattern, the age of the user, and the gender of the user, the system can detect early onset of illness and notify the user accordingly. As an example, this may include characteristics or changes identified by comparison to that particular user's historic data, or comparison to data collected from a variety of users having similar characteristics as that particular user, or both.

FIG. 1 schematically illustrates an end-to-end illness data collection and processing system 100 in accordance with one non-limiting embodiment. Such illness data can be utilized to track and analyze diurnal curves of users in accordance with the present disclosure. The system 100 can comprise a temperature sensing probe 102 (e.g. a medical thermometer, a wearable device with on-board temperature sensor, etc.) communicatively coupled with an auxiliary user device 104 (e.g. smartphone, tablet, computer, etc.). The temperature sensing probe 102 may include a temperature sensor, and in some implementations may include a processor, memory, communication device, and other components as may be required to measure, interpret, and transmit temperature data. The auxiliary user device 104 being coupled with one or more servers 108, such as one or more cloud servers, virtual servers, physical servers, or other computing environments, through network connections. Each server 108, and each auxiliary user device 104, may have one or more processors, communication devices, storage devices or other components as may be necessary to receive, transmit, store, analyze, and manipulate information. In some embodiments, a user can provide various data related to the user's health and/or other demographic information into to the auxiliary user device 104. In some instances, users can set up a profile with additional contextual data associated with each profile, such as the age and gender the user. Some temperature datasets, such as a diurnal curve, may be based in part on the user's age and gender. As described below, deviations from the expected shape of a particular user's diurnal curve, such as an inversion, or other deviations present in a temperature dataset, can be a leading indicator of illness. Additionally or alternatively, based on the temperature dataset analysis provided herein, the probability of detecting a true fever for a user during a febrile episode can be determined and provided to the user or other recipient. Additionally or alternatively, based on the temperature dataset analysis provided herein, the cutoff temperature for when febrile illness is identified can be adjusted based on age and gender, as well as the time of date the temperature was obtained, in addition to any other factors that may be provided by the user, determined by the auxiliary user device 104, or otherwise determined.

User data, including temperature readings can be transmitted to the server 108 by the auxiliary user device 104. In some cases, temperature sensing probe 102 may be configured to transmit data directly to the server 108 without the aid of the computing device 104. In any event, the server 108 can be configured to store various types of data transmitted from the computing device 104 or the temperature sensing probe 102 in one or more databases 110 of a data infrastructure 118. Data provided to the data infrastructure 118 can include the time of day that the individual took their temperature with the temperature sensing probe 102, the location of the individual at the time of measurement (e.g., based upon a global positioning satellite signal or other location signal from the auxiliary user device 104), the individual's heart rate at the time of measurement (e.g., based upon a measurement by a heart rate monitor of the auxiliary user device 104), and any indications of recent physical activity by the user (e.g., an indication from the auxiliary user device 104 that the individual was recently performing a strenuous exercise, which may be determined based upon measurements by an accelerometer, step counter, or other sensor). Thus, the temperature sensing probe 102 of FIG. 1 allows for the collection of temperature data points over time (or continuous measurement) such that a temperature dataset of a particular user of the system can be tracked and associated with other data over that period of time (e.g., the exact time of a particular measurement, or other characteristics present during that measurement such as high ambient heat or strenuous activity). This temperature dataset may be expressed as a diurnal curve or other data structure, and may be used for comparison, analysis, and other activities a will be described in more detail below.

The data infrastructure 118 can also include various engines to process the data, such as analysis engine 112, and various techniques for allowing access to, or otherwise report data, such as user APIs 114. As illustrated, the APIs 114 can allow for the presentation of data on a user application 116, for example. It is to be appreciated, however, that any suitable technique can be used to transmit information from the data infrastructure 118 to a user application 116. Additionally, in some embodiments, other data sets, shown as third party data 106, which are not generated by the temperature sensing probes 102, can also be ingested by the server 108. For example, the server 108 can retrieve web data from the Centers for Disease Control and Prevention's (CDC's) Weekly U.S. Influenza Surveillance Report, or data from other data sources.

In accordance with one or more implementations, in order to increase accuracy, a server can perform a quality check to discard any data points that are invalid, not useful, or likely erroneous in some way. For instance, if a temperature reading collected by the temperature sensing probe 102 is outside of human body temperature range, a rule can be applied to discard those individual readings. After initial clean up, and the performance of any other pre-processing steps, individual-level temperature datasets (e.g., diurnal curves or other expressions of temperature relative to time or other characteristics) can be derived from the raw data collected from the smart thermometers. An analysis of the temperature dataset can be performed to assess and detect whether the individual is ill, or provide other types of dataset based analysis. As provided by FIG. 2-11, which each show temperature datasets expressed as diurnal curves, such assessment can be based on the age and gender of the user, among other factors. Changes in the shape of the diurnal curves, such as an inversion, can indicate the presence or absence of illness. Notably, such change in diurnal curves may occur prior to the user actually presenting with a fever. While FIG. 2-11 show temperature datasets expressed as diurnal curves, it should be understood that the systems and methods disclosed herein may be implemented to express and analyze temperature datasets in varying ways in addition to or as an alternative to the use of diurnal curves.

Figure 2:
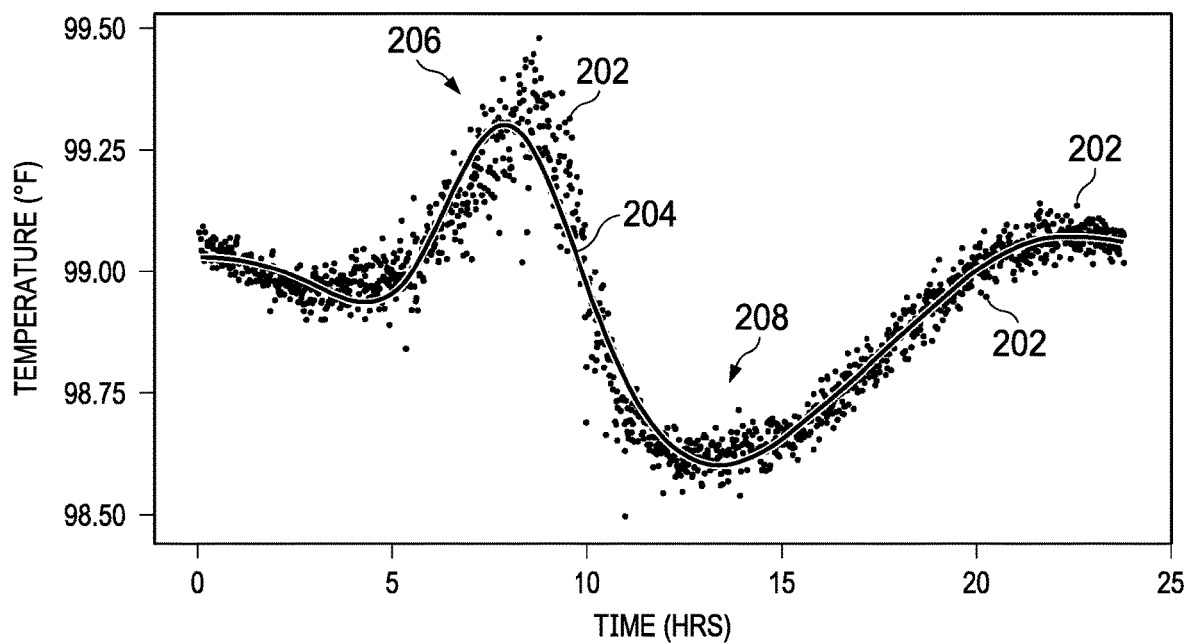
FIG. 2 illustrates a trend line of temperature readings from a plurality of users over a 24-hour period.

Referring now to FIG. 2, a plot 200 shows temperature readings 202 that were collected by the system 100 of FIG. 1 from numerous individuals. It is noted that the temperature readings 202 were typically collected from the individuals while they was experiencing a fever or other illness related symptoms. Each individual temperature reading 202 in FIG. 2 is plotted against the time of day at which the temperature reading was collected by the temperature sensing probe 102 (FIG. 1), with X-axis originating at midnight. A trend line 204 of the individual temperature readings 202 reveals a diurnal temperature curve having an initial peak followed by a valley 208.

Figure 3:
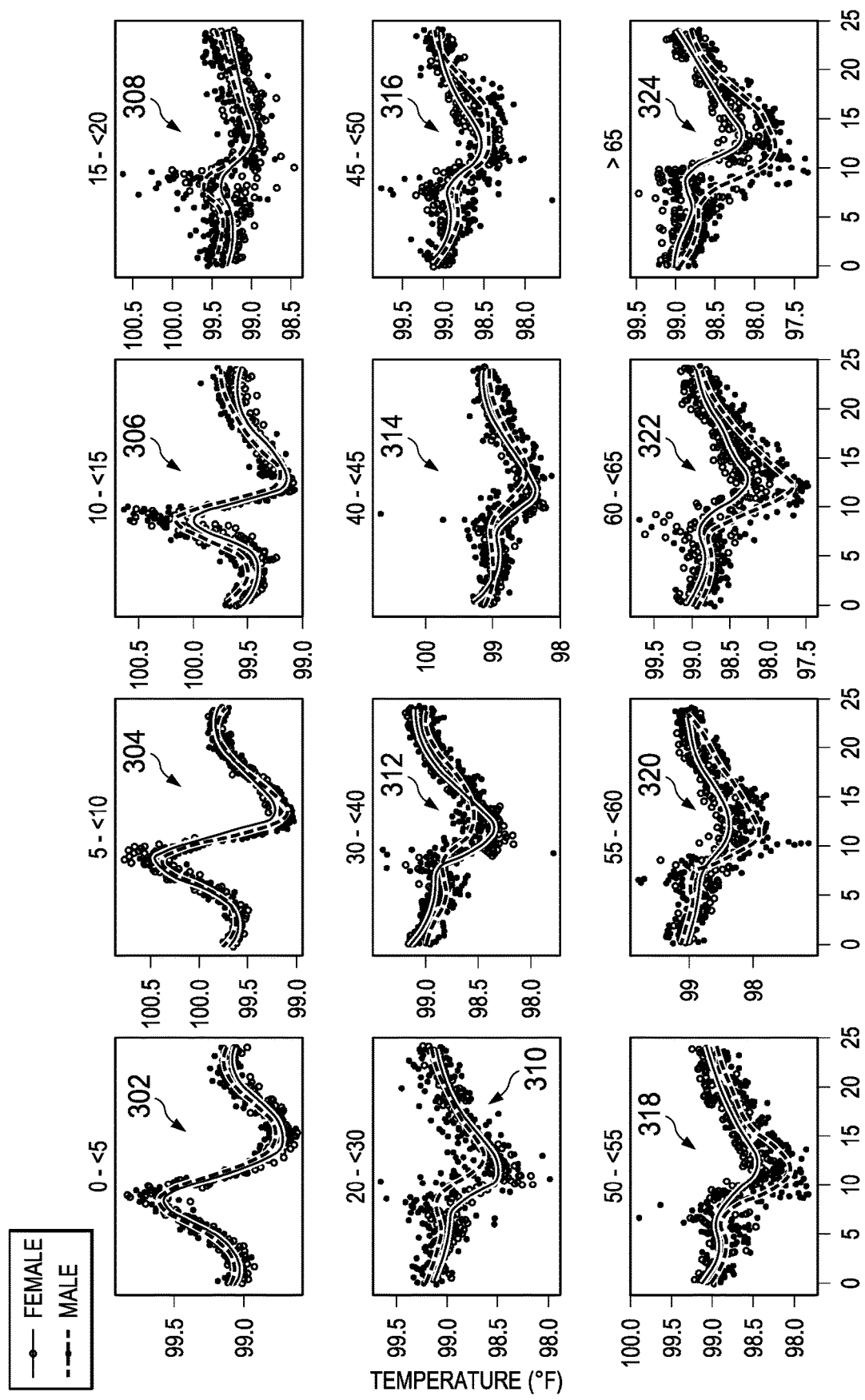
FIG. 3 are plots of temperature data points from users over time identified as having a fever at the time of the temperature measurement, separated by age and gender.

While FIG. 2 shows an example plot of data points across all users of the system 100, FIG. 3 provides a series of plots 302-324 that separate the data points based on both age group and gender. Similar to the data set plotted in FIG. 2, it is noted that the data points plotted in FIG. 3 are from users of the system 100 that were identified as having a fever. As shown, plot 302 includes data points collected by the temperature sensing probe 102 by users between the ages of 0-5 years old. Plot 304 includes data points collected by the temperature sensing probe 102 by users between the ages of 5-10 years old. Plot 306 includes data points collected by the temperature sensing probe 102 by users between the ages of 10-15 years old. Plot 308 includes data points collected by the temperature sensing probe 102 by users between the ages of 15-20 years old. Plot 310 includes data points collected by the temperature sensing probe 102 by users between the ages of 20-30 years old. Plot 312 includes data points collected by the temperature sensing probe 102 by users between the ages of 30-40 years old. Plot 314 includes data points collected by the temperature sensing probe 102 by users between the ages of 40-45 years old. Plot 316 includes data points collected by the temperature sensing probe 102 by users between the ages of 45-50 years old. Plot 318 includes data points collected by the temperature sensing probe 102 by users between the ages of 50-55 years old. Plot 320 includes data points collected by the temperature sensing probe 102 by users between the ages of 55-60 years old. Plot 322 includes data points collected by the temperature sensing probe 102 by users between the ages of 60-65 years old. Plot 324 includes data points collected by the temperature sensing probe 102 by users older than 65 years old.

Figure 4:
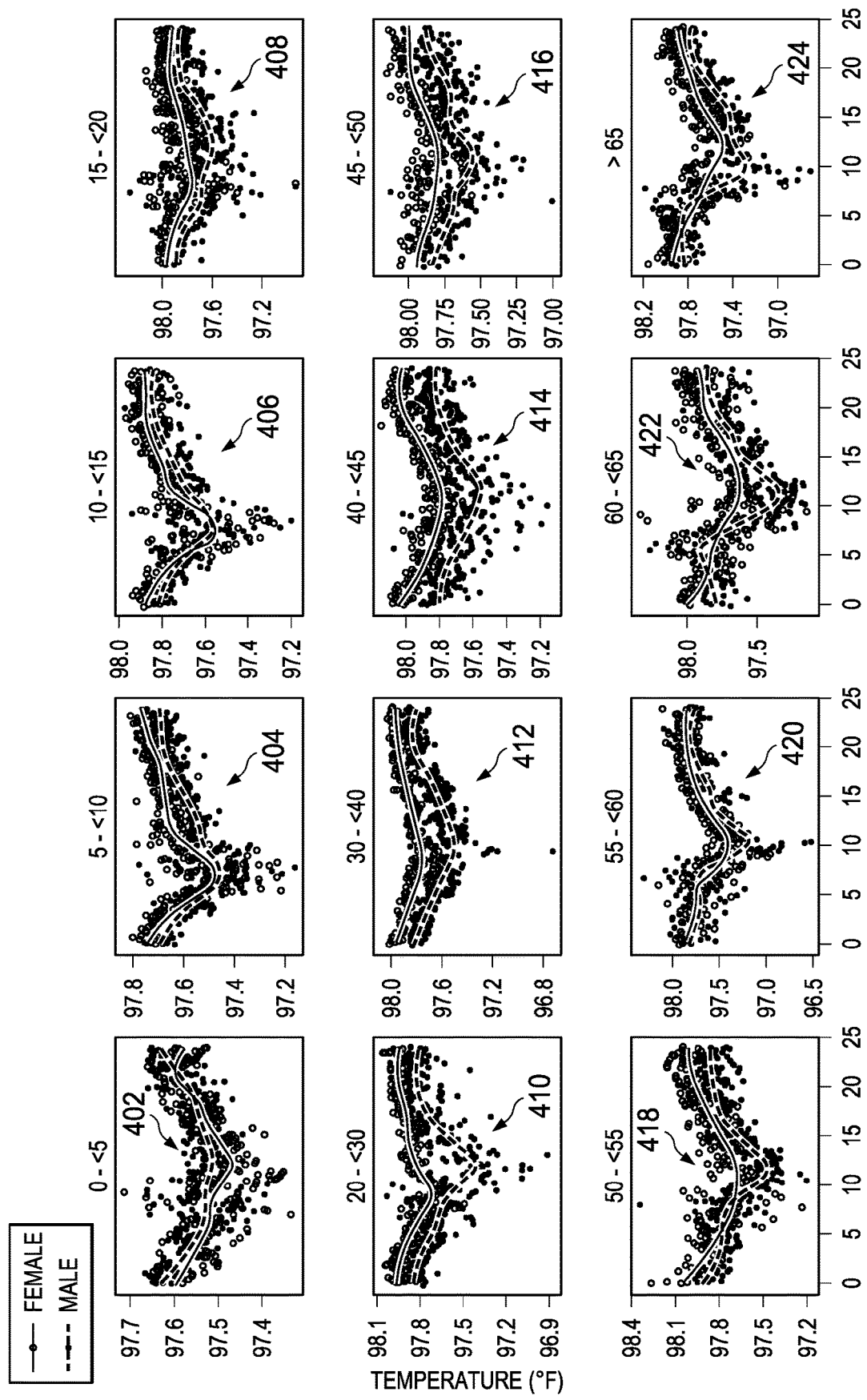
FIG. 4 are plots of temperature data points from users over time identified as not having a fever at the time of the temperature measurement, separated by age and gender.

FIG. 4 provides another series of plots 402-424 that separate the data points based on age group and gender. The data points plotted in FIG. 4, however, are from users of the system 100 that were identified as not having a fever. As shown, plot 402 includes data points collected by the temperature sensing probe 102 by users between the ages of 0-5 years old. Plot 404 includes data points collected by the temperature sensing probe 102 by users between the ages of 5-10 years old. Plot 406 includes data points collected by the temperature sensing probe 102 by users between the ages of 10-15 years old. Plot 408 includes data points collected by the temperature sensing probe 102 by users between the ages of 15-20 years old. Plot 410 includes data points collected by the temperature sensing probe 102 by users between the ages of 20-30 years old. Plot 412 includes data points collected by the temperature sensing probe 102 by users between the ages of 30-40 years old. Plot 414 includes data points collected by the temperature sensing probe 102 by users between the ages of 40-45 years old. Plot 416 includes data points collected by the temperature sensing probe 102 by users between the ages of 45-50 years old. Plot 418 includes data points collected by the temperature sensing probe 102 by users between the ages of 50-55 years old. Plot 420 includes data points collected by the temperature sensing probe 102 by users between the ages of 55-60 years old. Plot 422 includes data points collected by the temperature sensing probe 102 by users between the ages of 60-65 years old. Plot 424 includes data points collected by the temperature sensing probe 102 by users older than 65 years old.

Figure 5:
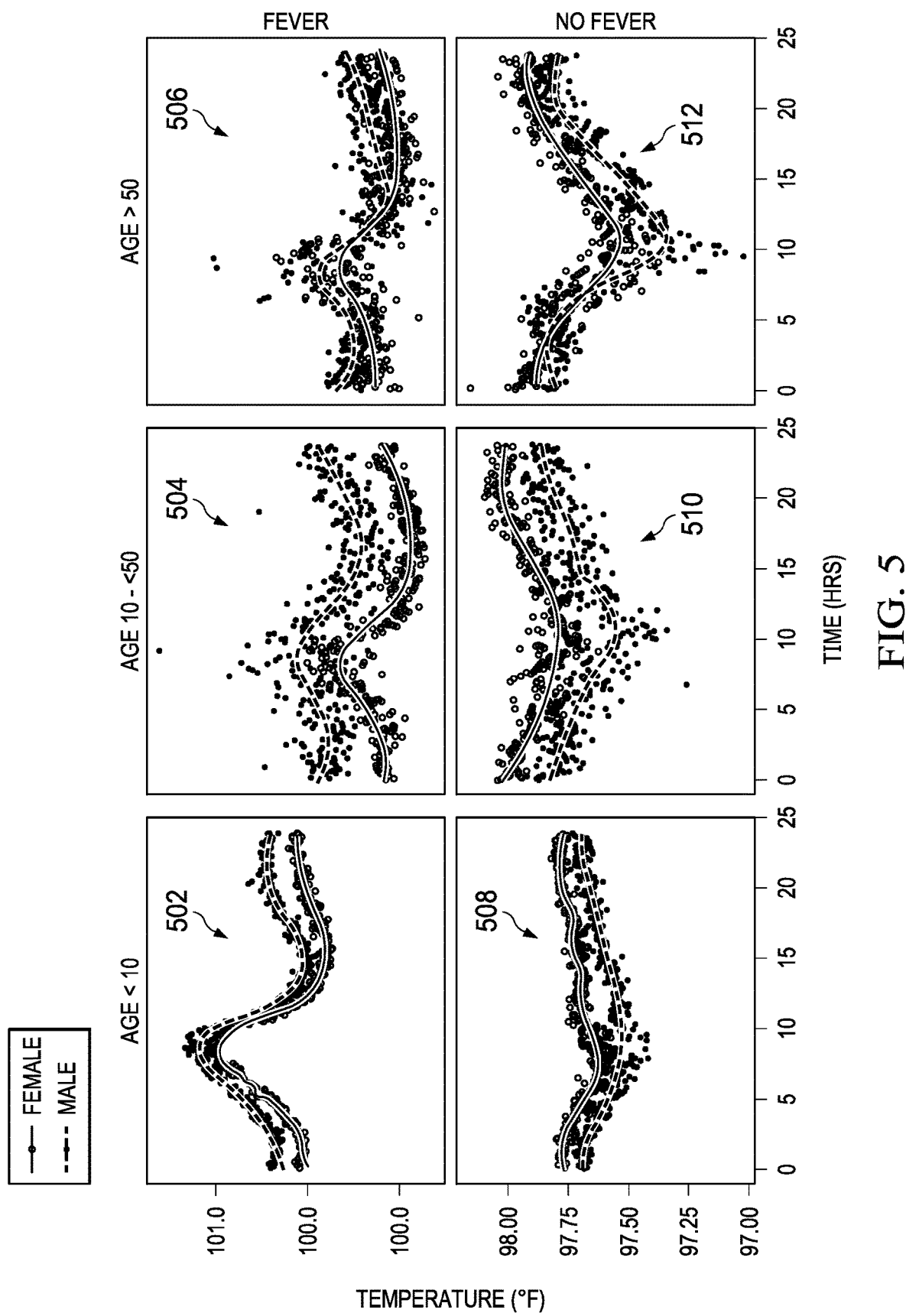
FIG. 5 are additional plots of temperature data points from users over time identified as having a fever at the time of the temperature measurement, separated by age and gender, and plots of temperature data points from users over time identified as not having a fever at the time of the temperature measurement, separated by age and gender.
Figure 6:
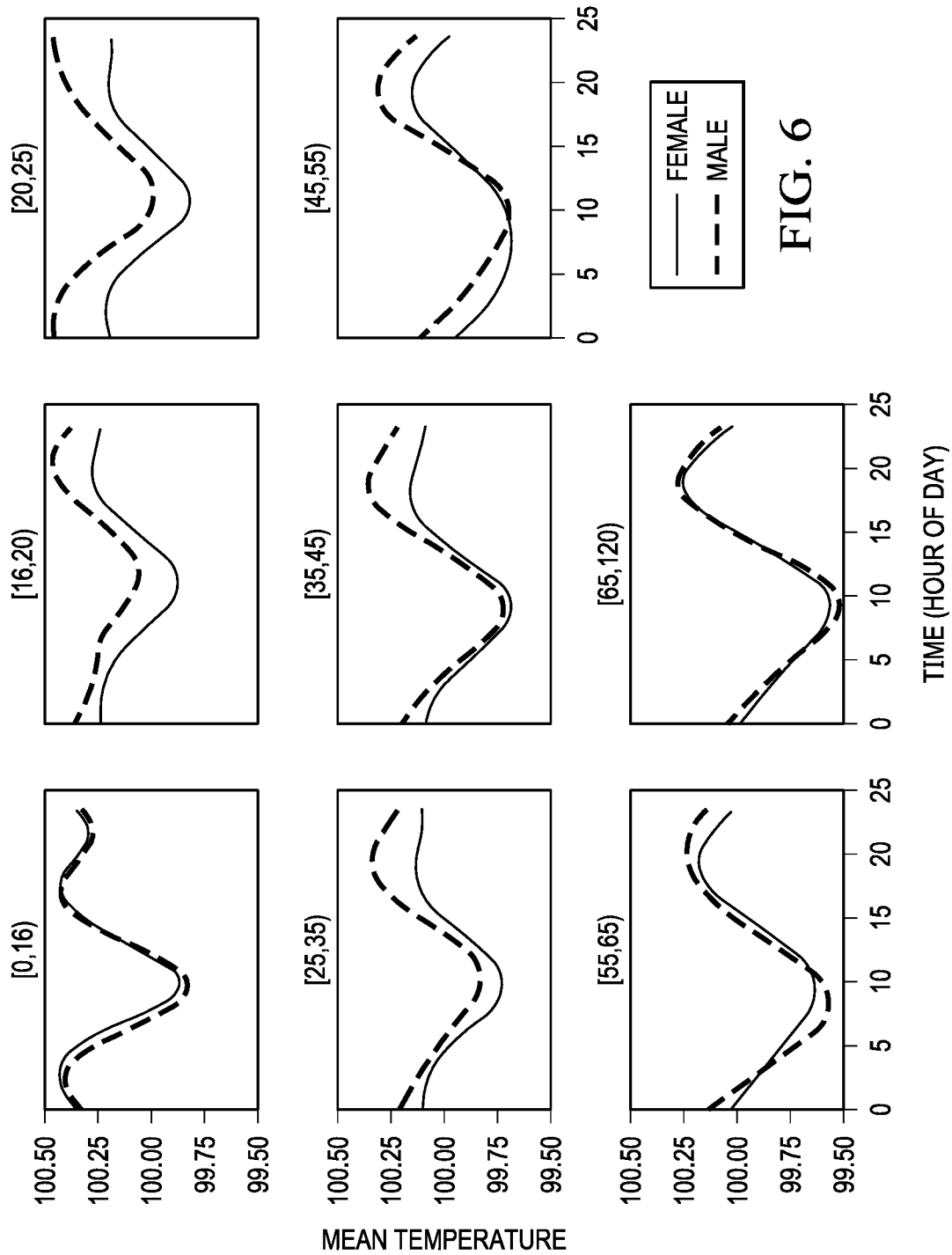
FIG. 6 are plots of temperature data points from users over time separated by age and gender with a cut-point of 12 hours.
Figure 7:
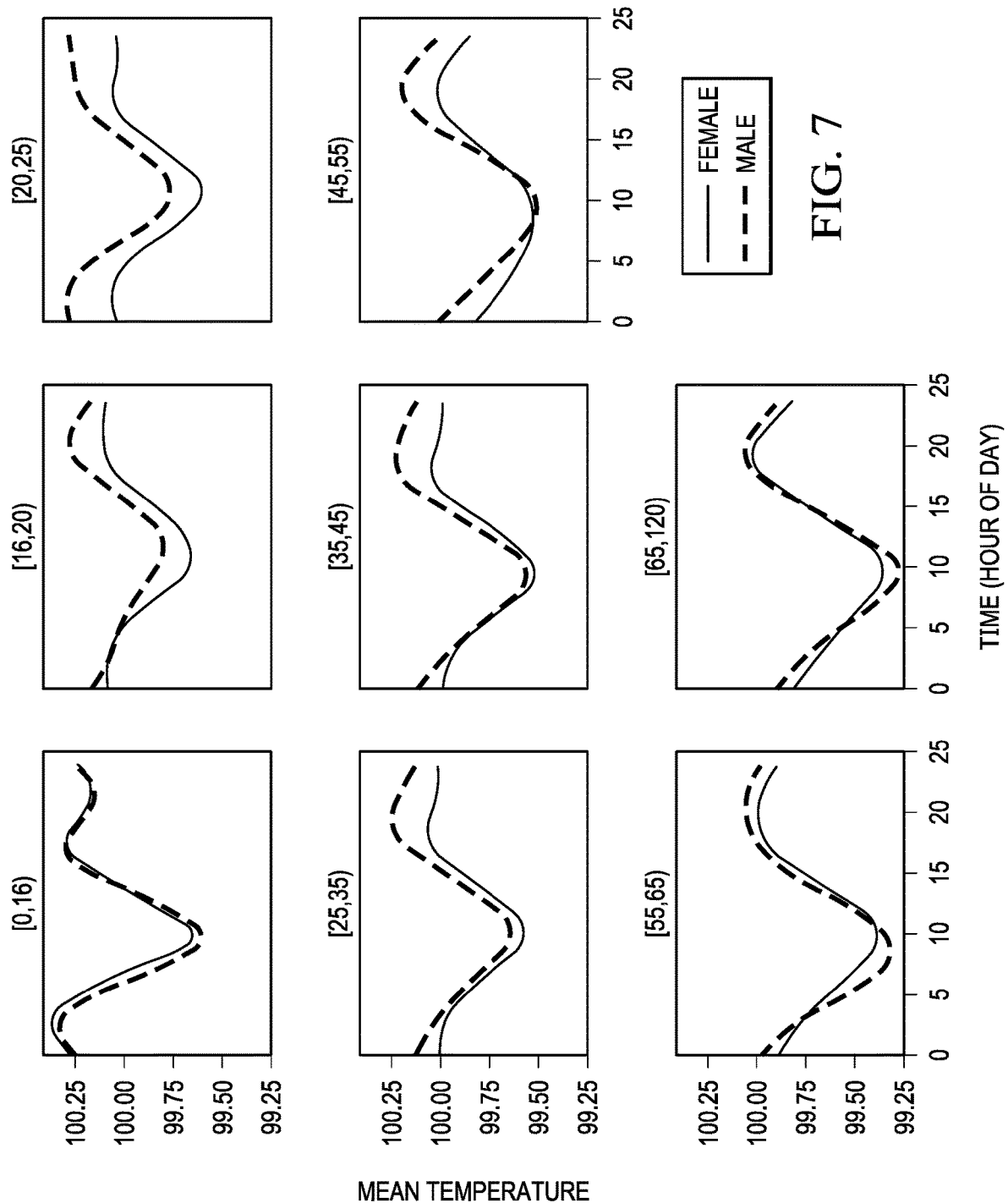
FIG. 7 are plots of temperature data points from users over time separated by age and gender with a cut-point of 36 hours.
Figure 8:
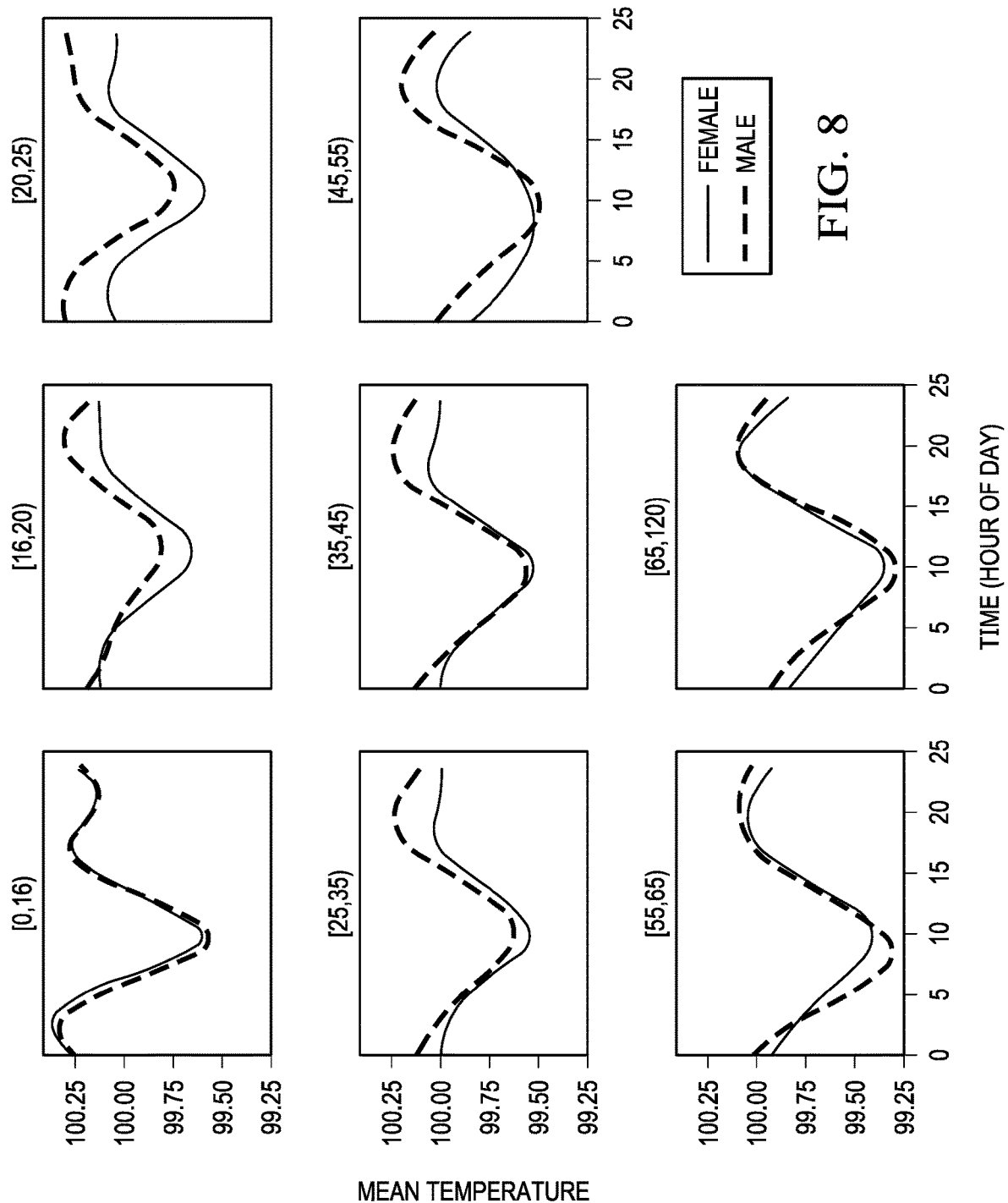
FIG. 8 are plots of temperature data points from users over time separated by age and gender with a cut-point of hours.
Figure 9:
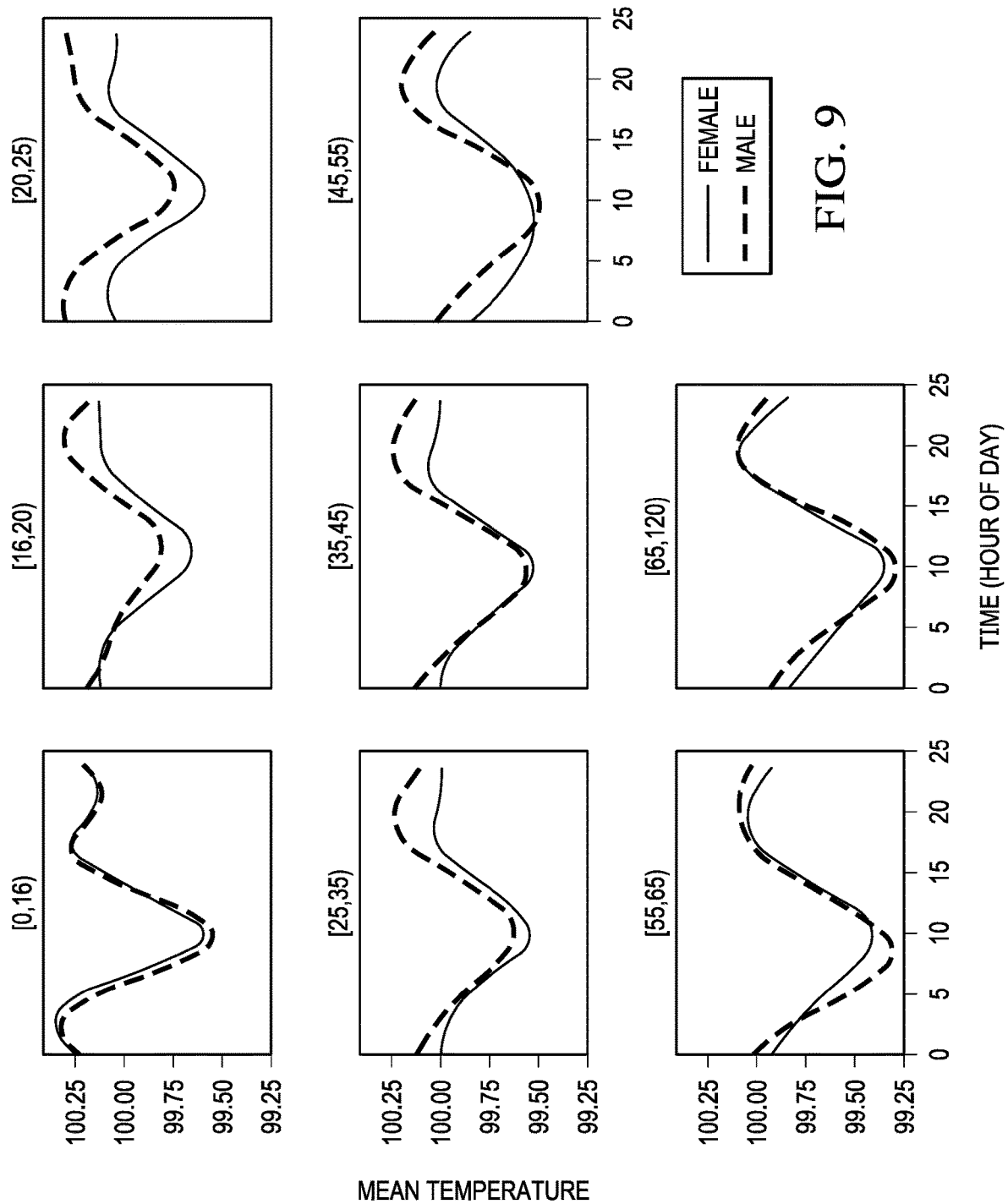
FIG. 9 are plots of temperature data points from users over time separated by age and gender with a cut-point of hours.

Referring now to FIG. 5, a first series of plots 502-506 shows users in three separate age groups that have a fever, with the data separated by gender in each plot. Plot 502 includes data points collected by the temperature sensing probe 102 by generally pre-pubescent users less than 10 years of age. Plot 504 includes data points collected by the temperature sensing probe 102 by users between the ages of 10 and 50, which are generally post-pubescent and generally pre-menopause. Plot 506 includes data points collected by the temperature sensing probe 102 by users that are older than 50 years of age. For comparison, a second series of plots 508-512 in FIG. 5 shows users in three separate age groups that do not have a fever. Plot 508 includes data points collected by the temperature sensing probe 102 by generally pre-pubescent users less than 10 years of age. Plot 510 includes data points collected by the temperature sensing probe 102 by users between the ages of 10 and 50, which are generally post-pubescent and generally pre-menopause. Plot 512 includes data points collected by the temperature sensing probe 102 by users older than 50 years of age.

In accordance with the present disclosure, diurnal curve patterns of groups of users can be grouped by age and gender, for example, for the purpose of modeling diurnal curve dynamics. In particular, diurnal curves are shown to have characteristics based on the user's age, gender, and whether they are healthy or not. As such, modeling in accordance with the present disclosure can be used, for example, to assist with identifying illness, infection, and so forth, based on the users' age, gender, and their diurnal curve as determined through multiple temperature readings over a period of time. In accordance with the present disclosure, detected changes in their diurnal curve, even before the onset of a fever, can be a leading indicator of illness or infection, for example.

In accordance with the present disclosure, the system can detect a change in a user's diurnal curve using any suitable approach. In a first embodiment, for example, an algorithm or routine can compare the actual diurnal curve of the user, as measured by the temperature sensing probe 102 over time, to an expected diurnal curve for a healthy user. As provided above, the expected diurnal curve can be based on, for example, the age and gender of the user. In accordance with some embodiments, the system can store a first set of expected male and female diurnal curves for users less than 10 years of age, a second set of expected male and female diurnal curves for users between the ages of 10 and 50, and a third set of expected male and female diurnal curves for users that are older than 50 years of age. As is to be appreciated, however, any number of expected diurnal curves for various user segments can be stored by the system without departing from the scope of the present disclosure.

Subsequent to the comparison of the actual diurnal curve to the expected diurnal curve based on the user's age and gender, a magnitude of the deviation between the two curves can be utilized to determine if the user is potentially ill. For instance, if the magnitude of the deviation exceeds a threshold amount, the user can be alerted (such as through a mobile application executing on the auxiliary user device 104) of their potential illness. In some embodiments, for example, the threshold for determining a fever can be set at about 1.8° F. above the baseline curve, as measured along the curve at the time the temperature for a particular user was collected. In other embodiments, the threshold for determining a fever can be set at about 2.0° F. above the baseline curve, as measured along the curve at the time the temperature for a particular user was collected. In some embodiments, the threshold for determining a fever can be anywhere in the range of about 1.8° F. to above 2.0° F. In some embodiments, the threshold for determining a fever can be set at a value below 1.8° F. or at a value above 2.0° F. Moreover, the threshold value can differ along the curve, such that different thresholds are used at different times of day. Additionally or alternatively, a first threshold can be utilized for a first group of users, while a second threshold can be utilized by a second group of users. The first group of users can be users within a first demographic, and the second group of users can be users with in a second demographic, for example. A user's demographic can be based on age, gender, and/or a combination thereof.

In accordance with another embodiment, the system can store a set of male and female diurnal curves for healthy users and a second set of male and female diurnal curves for ill users for each of a plurality of different age segmentations. Based on a user's age and gender, the system can compare the actual diurnal curve of the user, as measured by the temperature sensing probe 102 over time (i.e., 3+ times over a 24 hour time frame), to the diurnal curve for healthy users and the diurnal curve for ill users. Depending on whether the actual diurnal curve is deemed to be statistically closer to the healthy diurnal curve or the ill diurnal curve, the system can assess whether the user may be potentially ill and the alert them, or take other action, as may be appropriate. In the above examples, storage of temperature datasets and analysis using temperature datasets can occur locally (e.g., on one or both of the auxiliary user device 104 and thermometer 102), remotely (e.g., on the data infrastructure 118), or both. As an example, an initial analysis may be performed by the auxiliary user device 104 immediately after new data is added to an individual's temperature dataset, where the new data may be compared to historic data for that individual and/or aggregate datasets from many other individuals, and the results of such analysis may be provided to that individual almost immediately after measurement (e.g., a notification that the user may be ill, and a suggestion to isolate, rest, and perform further measurements). A deeper analysis may be performed in parallel by the data infrastructure 118, which may compare the new data points to a larger comparison dataset, and may use more sophisticated methods of comparison (e.g., artificial intelligence) in order to provide a more thorough analysis to confirm or modify the earlier local analysis.

Referring now to modeling diurnal curves or other temperature datasets, in general, the mean temperature in the diurnal curve decreases with age. To estimate mean temperature for modeling, a least-squares regression model can be used with a sinusoidal time component and interaction terms for age group and gender. In some embodiments, four sinusoids are used: sine and cosine terms with 12-hour periodicity, and sine and cosine terms with 24-hour periodicity, although this disclosure is not so limited. This approach can match the oscillating pattern observed in the descriptive plots, while enforcing periodicity. Each of these four terms are interacted with age group and gender, which are also interacted with each other.

To estimate the probability of recording a fever during a given time period, a generalized linear model with a log-link and binomial distribution can be used, along with the same sinusoidal component as the mean temperature model, interacted with age and gender. Finally, both the mean temperature curve and the probability of recording a fever for a representative healthcare population can be estimated. Parameter estimates can be weighted using the breakdown of age-specific employment percentages from the Bureau of Labor Statistics, for example, and use the delta method to estimate the confidence interval around these estimates.

Figure 10:
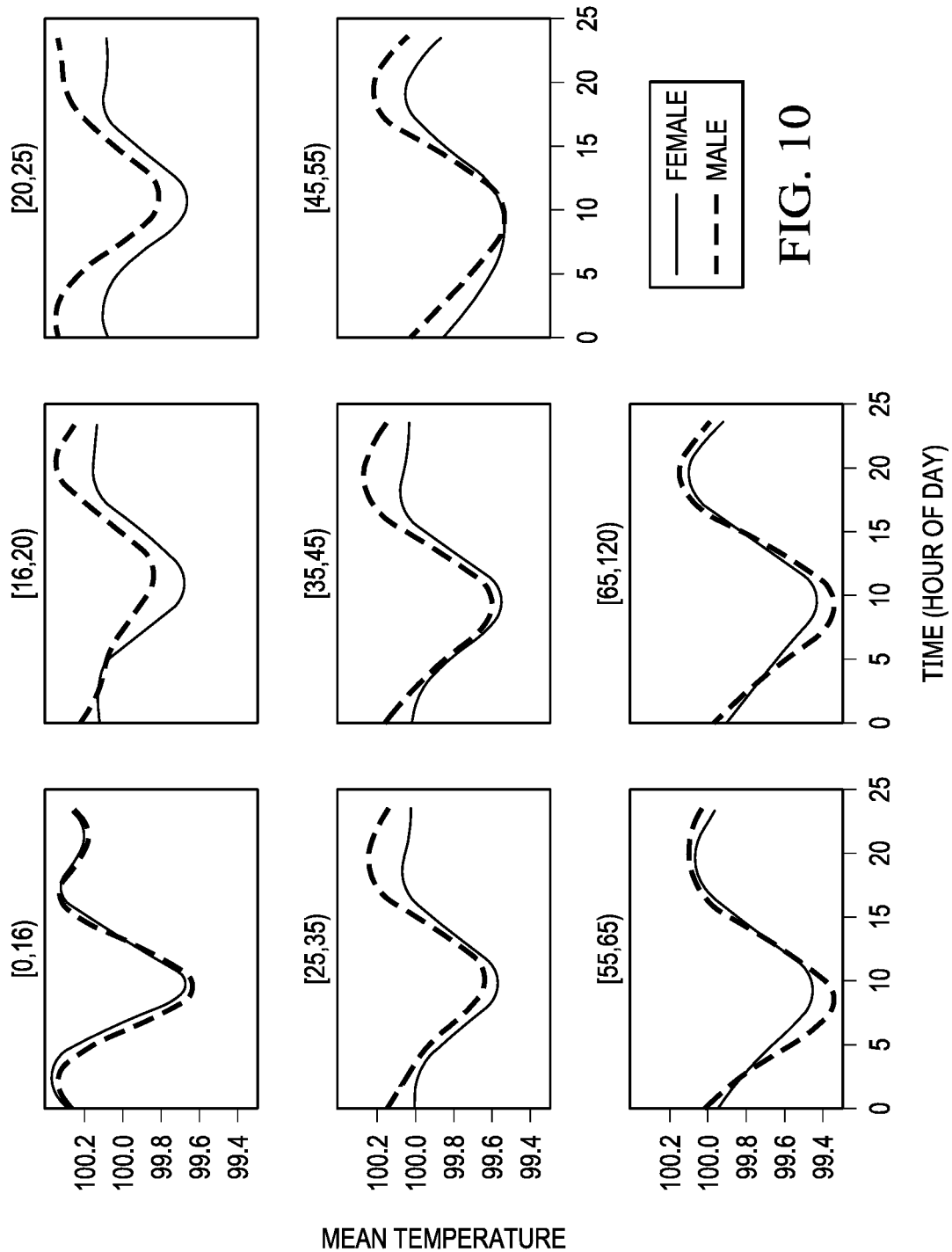
FIG. 10 depict diurnal patterns for different age groups and separated by gender.

Thus, in accordance with present disclosure, a sinusoidal model can by utilized to estimate the mean diurnal pattern by time of day, while controlling for age and gender. The diurnal pattern for different age groups and by gender is depicted in FIG. 10. Similar to the univariate descriptive plots for all demographics, temperature during an illness episode tends follow a cyclical pattern. Mean temperatures decrease until a certain point in the morning, hitting a trough, and then increasing until a certain point in the evening, hitting a peak. The overall curve tends to be lower for those in more advanced age groups, while for males age 16-55, mean temperature throughout the day tends to be higher than that of females. This does not appear to be the case for individuals younger than 16 or older than 55.

In accordance with the present disclosure, illness episodes can be constructed using a variety of approaches. In some embodiments, for example, illness episodes can be constructed by first grouping temperature readings into clusters of activity that are likely to represent a period of illness in a particular device user. Temperature readings recorded over a series of days can be collapsed and these episodes can be used to identify illness duration, household transmission events, and biphasic fever patterns (two distinct febrile episodes that occurred in short succession), for example. Notably, each of these illness patterns are also shown to be highly correlated with influenza-like-illness activity.

In accordance with some forms of modeling, all readings recorded by the same user profile on a particular temperature sensing probe 102 (FIG. 1) that occur within a fixed interval of another reading can be grouped into an episode. For example, 24 hours can be used as the maximum time between readings to define an episode, although this disclosure is not so limited. Because some users may take recurrent readings on a regular basis (e.g., fertility planning), episodes that last longer than a typical illness can be excluded (i.e., 7 days). Illness episodes can be defined, for example, as the episodes where at least one fever was recorded during the episode interval. Various analysis in accordance with the present disclosure can describe diurnal temperature patterns among readings in these identified illness episodes, for example.

In order to analyze the sensitivity of the results to the way in which illness episodes are defined, a sensitivity analysis can be performed by varying the cut-point to determine the end of an illness episode. For example, the cut-point can be varied from 24 hours, and both mean temperature analysis and fever probability analysis can be repeated with cut-points of 12, 36, 48, and 72 hours. Example model predictions for each of these cut-points can be seen in FIG. 6-9, respectively. While there are slight variations in the model predictions when varying the cut-point used to identify an illness episode, there are no significant departures from the patterns observed and described for the 24-hour cut-point model. Furthermore, the general pattern remains consistent across gender and age groups, and the probability of drawing a fever is roughly the same across specifications.

Figure 11:
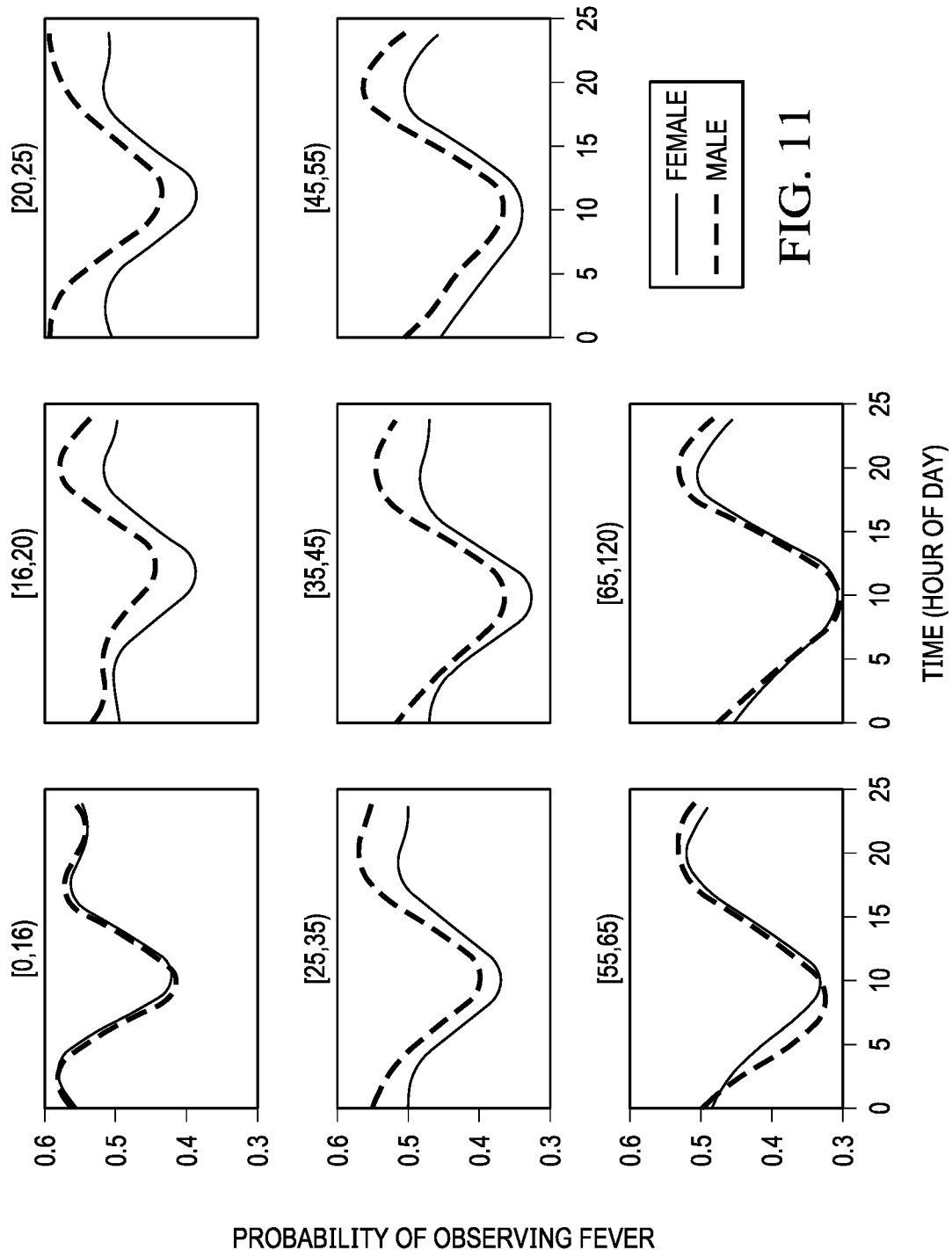
FIG. 11 are plots providing the probability of observing a fever during a given time of the day, separated by age group and gender.

The probability of observing a fever during a given time of the day, for example, can also be estimated in accordance with the present disclosure. To estimate the probability of observing a fever, a generalized linear model can be used with a logit link and binomial distribution, although this disclosure is not so limited. Referring now to FIG. 11, fitted values for each time period are plotted by age group and gender using the sinusoidal time component. Consistent with the mean temperature model, the diurnal pattern varies in a cyclical form with the time of day.

Depending on the particular age and gender of an individual, the probability of recording a fever during an illness episode may vary considerably by the time of the day, where recording a fever includes accurately measuring the individual's temperature as greater than 100° F. Thus, based on a large collection of thermometer readings from thermometers in accordance with the present disclosure, variation in temperature readings among subjects during a febrile episode can be seen. Based on those readings, temperature patterns follow a distinct diurnal pattern, and thus the likelihood of recording a fever (e.g., temperature >100° F.), also varies. The likelihood not only varies by time, but also by age and gender. For temperature data collected by the temperature sensing probe 102, for example, the systems and methods described herein can provide population-based estimates of the probability, given a febrile episode, that an individual of a given age and gender may present with a measurable fever at a particular time. By way of example and referring to FIG. 11, a male individual over the age of 65 years that is currently suffering from a febrile illness has a 30% chance of measuring above 100° F. at around 9:00 am, and a 55% chance of measuring above 100° F. at 8:00 pm.

Figure 12:
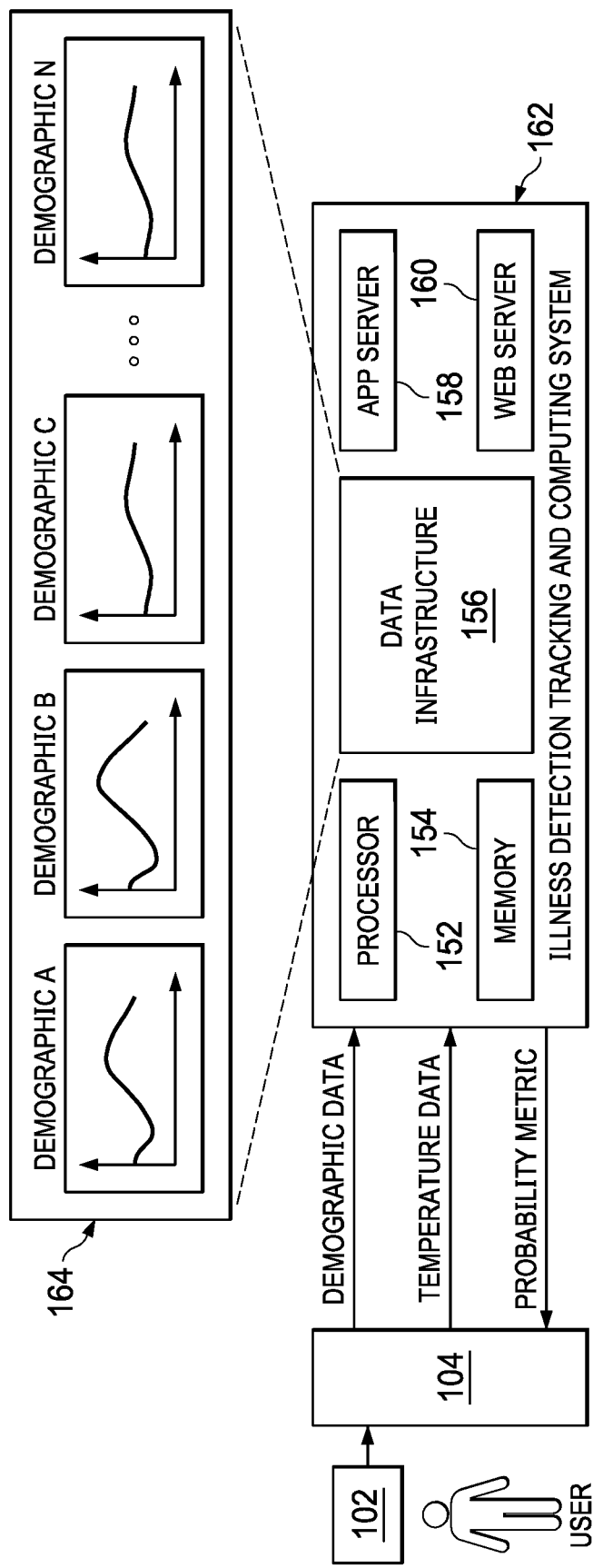
FIG. 12 schematically illustrates an operational example of identifying a diurnal curve probability model from a plurality of diurnal curve probability models to apply to a temperature reading of a particular user.

Referring now to FIG. 12, an operational example is schematically illustrated. A temperature of a user is depicted being obtained by the temperature sensing probe 102 of FIG. 1. The temperature reading can be transmitted to an illness detection tracking and computing system 162 by an auxiliary user device 104 or, in some cases, the temperature sensing probe 102 may be configured to transmit data directly to the illness detection tracking and computing system 162 without the aid of the computing device 104.

In some embodiments the illness detection tracking and computing system 162 can provide the same or similar functionality as the server 108 and associated data infrastructure 118 as illustrated in FIG. 1 and can be provided using any suitable processor-based device or system, such as a personal computer, laptop, server, mainframe, or a collection (e.g., network) of multiple computers, for example. The illness detection and tracking computing system 162 can include one or more processors 152 and one or more computer memory units 154. For convenience, only one processor 152 and only one memory unit 154 are shown in FIG. 12. The processor 152 can execute software instructions stored on the memory unit 154. The processor 152 can be implemented as an integrated circuit (IC) having one or multiple cores. The memory unit 154 can include volatile and/or non-volatile memory units. Volatile memory units can include random access memory (RAM), for example. Non-volatile memory units can include read only memory (ROM), for example, as well as mechanical non-volatile memory systems, such as, for example, a hard disk drive, an optical disk drive, etc. The RAM and/or ROM memory units can be implemented as discrete memory ICs, for example.

The memory unit 154 can store executable software and data for the illness detection and tracking computing system 162. When the processor 152 of the illness detection and tracking computing system 162 executes the software, the processor 152 can be caused to perform the various operations of the illness detection and tracking computing system 162. Data used by the illness detection and tracking computing system 162 can be from various sources, such as a data infrastructure 156 having one or more databases, which can be an electronic computer databases, for example. The data stored in the data infrastructure 156 can be stored in a non-volatile computer memory, such as a hard disk drive, a read only memory (e.g., a ROM IC), or other types of non-volatile memory. In some embodiments, one or more databases of the data infrastructure 156 can be stored on a remote electronic computer system, for example. As is to be appreciated, a variety of other databases, or other types of memory storage structures, can be utilized or otherwise associated with the illness detection and tracking computing system 162.

As shown in FIG. 12, the illness detection and tracking computing system 162 can include several computer servers. For example, the illness detection and tracking computing system 162 can include one or more application servers 158, web servers 160, and/or any other type of servers. For convenience, only one application server 158 and one web server 160 are shown in FIG. 12, although it should be recognized that the disclosure is not so limited. The servers can cause content to be sent to the computing device 104 and/or other recipient computing systems in any number of formats, such as text-based messages, multimedia message, email messages, smart phone notifications, web pages, and so forth. The servers 158 and 160 can comprise processors (e.g., CPUs), memory units (e.g., RAM, ROM), non-volatile storage systems (e.g., hard disk drive systems), etc.

The web server 160 can provide a graphical web user interface through which various users of the system can interact with the illness detection and tracking computing system 162. The web server 160 can accept requests, such as HTTP requests, from clients (such as via a web browser on the computing devices 104, for example), and serve the clients responses, such as HTTP responses, along with optional data content, such as web pages (e.g., HTML documents) and linked objects (such as images, video, and so forth).

The application server 158 can provide a user interface for users who do not communicate with the illness detection and tracking computing system 162 using a web browser. Such users can have special software installed on their computing devices 104 that allows them to communicate with the application server 160 via a communication network. Such software can be downloaded, for example, from the illness detection and tracking computing system 162, or other software application provider, over a communication network to such computing devices.

Embodiments of the illness detection and tracking computing system 162 can also be implemented in cloud computing environments. "Cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

In addition to the temperature data being transmitted to an illness detection tracking and computing system 162 by an auxiliary user device 104 additional data regarding the user can also be provided. As schematically shown in FIG. 12, demographic data can be supplied to the illness detection tracking and computing system 162. Demographic data can include, for example, the user's gender and the user's age. As is to be appreciated, the demographic data can be supplied to the illness detection tracking and computing system 162 concurrently with the temperature data, or it can be provided to the illness detection tracking and computing system 162 as part of a user profile, or provided via other suitable data ingestion process, for example.

As schematically shown, the illness detection tracking and computing system 162 can store a plurality of diurnal curve probability models 164 or other temperature datasets, which can each correspond to a particular demographic or other characteristic, as described above. Based on data associated with the user, such as age and gender, the illness detection tracking and computing system 162 can determine which of the stored diurnal curve probability models 164 or other temperature datasets is applicable to the user. Once the stored diurnal curve probability model has been identified, the time of day the temperature reading was obtained can be used by the illness detection tracking and computing system 162 to determine the probability of detecting a fever of the user during an illness episode. By way of example, a male individual over the age of 65 years has around a 30% chance of registering a fever at around 9:00 am but a 55% chance of registering a fever at 8:00 pm (see e.g., FIG. 11). An indication of such probability can be provided by the illness detection tracking and computing system 162 to the user, such as through the computing device 104, in any suitable format. As an example, this could include the auxiliary user device 104 providing an indication after a recent measurement by the thermometer 102 of the results of such measurement, as well as the probability that a febrile illness might be present despite the recent measurement not indicating a fever, or the probability that there may be no febrile illness despite the recent measuring indicating a fever. The auxiliary user device 104 may be further configured to perform automatic temperature measurements, or to provide suggestions to a user to perform a manual temperature measurement, during a time of day or when other characteristics are present that will maximize the probability of detecting a febrile illness (e.g., following the above example, an automated notification at 8:00 pm suggesting that the user measure their temperature with the thermometer 102).

In some embodiments, such indication of probability of can alternatively or additionally be provided to another recipient, such as a medical professional, a screener, or an operator using the temperature sensing probe 102 to screen others for illness, for example. As such, in addition to submitting temperature information collected using the temperature sensing probe 102 to the illness detection tracking and computing system 162, the operator can also submit supplementary information regarding the person from which the temperature was collected (such as age and gender). Based on the age and gender of the person, the illness detection tracking and computing system 162 can identify an applicable diurnal curve probability model or other temperature dataset for the person being screened by the operator. Then, in view of the applicable diurnal curve probability model or other temperature dataset, and the time of day the operator obtained the temperature from the person or other characteristics, the illness detection tracking and computing system 162 can determine the probability of detecting a fever during an illness episode for that person. Such determination can be presented in any suitable fashion to the screener or other recipient, such as in the form of a confidence score or other metric.

Figure 13:
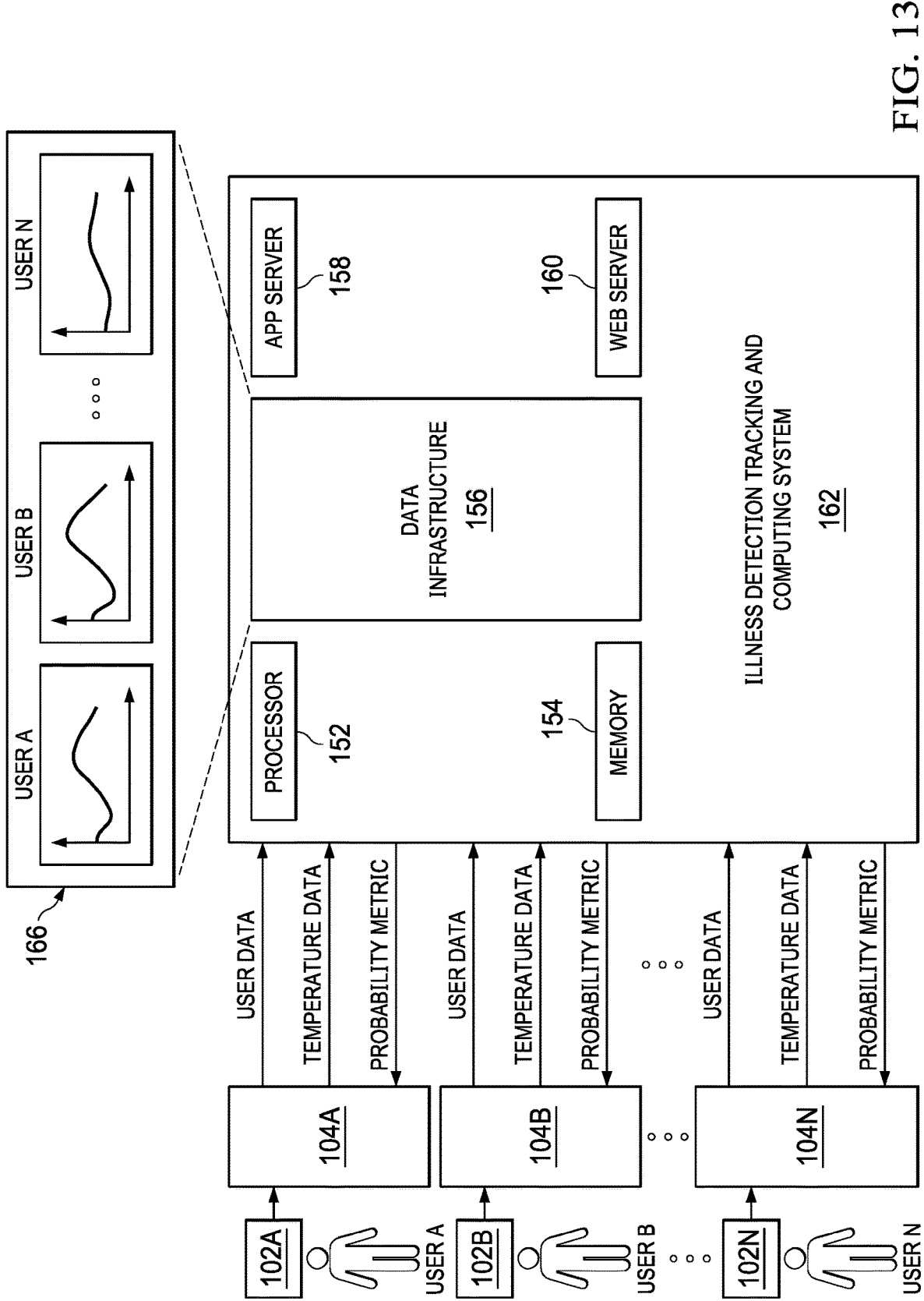
FIG. 13 schematically illustrates an operational example of generating baseline diurnal curves based on user data and subsequently using the baseline diurnal curves for temperature reading analysis.

Referring now to FIG. 13, in accordance with various embodiments, temperature datasets such as diurnal curves for specific individual users can be generated based on the user's historical data and then used as a baseline for analysis of subsequent temperature readings from that particular user. By way of example, when the users A-N are healthy, each user can utilize the temperature sensing probes 102A-N to submit a series of temperature readings over a period of time to the illness detection tracking and computing system 162, schematically illustrated as 'User Data' in FIG. 13. For instance, each of the users A-N can submit their temperature reading when they wake up and then continue to submit their temperature at various intervals and/or at specific times throughout the day via their temperature sensing probes 102A-N. The users 102A-N can follow this routine over a certain period of time, such as a 2-3 days, for example. In some embodiments, for example, a mobile application executing on the computer user device 104A-N can indicate to the users 102A-N when temperature readings should be obtained. Alternatively, continuous temperature monitoring over a period of time for a user can be performed by a wearable temperature sensing probe, or other type of suitable temperature collection device.

Based on the temperature readings collected for each user by their temperature sensing probe over time, baseline temperature datasets such as diurnal curves 166 for each particular user can be generated by the illness detection tracking and computing system 162, in accordance with the presently disclosed systems and methods. In this example, these baseline diurnal curves for the associated user A-N can beneficially be used by the illness detection tracking and computing system 162 for future analysis of temperature readings submitted by each respective user. As such, in accordance with various embodiments, subsequent temperature readings for that user can be compared to their own baseline diurnal curve for the purposes of identifying changes to the diurnal curve, which may be indicative of illness. Additionally or alternatively, the server 108 can determine the probability of detecting a fever during an illness episode for that user based on their baseline diurnal curve and the time of date of the temperature reading.

In some embodiments, a cutoff temperature (sometimes referred to as a threshold temperature, as described above) for when febrile illness is identified can be adjusted based on age and gender, as well as the time of date the temperature was obtained, based on the diurnal curve of the user. The applicable diurnal curve for the user can be, for example, a diurnal curve that is modeled based on the user's age and gender, or other characteristics. Additionally or alternatively, the applicable diurnal curve can be the baseline diurnal curve for the user, as described above. In any event, the cutoff temperature for when febrile illness is identified can vary throughout the day. By way of example, the cutoff or threshold temperature for determining whether a user's temperature is identified as febrile illness can be lower in the morning and higher at a later point in the day. In some embodiments, for example, the cutoff temperature may vary between about 1.8° F. and about 2.0° F. throughout the day.

In accordance with various embodiments of the present disclosure, temperature dataset tracking and/or modeling can also be used in the pre-test evaluation of a user being subjected to various types of medical diagnostic testing. By way of example, temperatures of individuals being tested for severe acute respiratory syndrome coronavirus 2 (SARS-CoV-2) are often taken as part of a pre-test evaluation. The presence of a fever can be to adjust pre-test probability, as those with fevers have an increased pre-test probability of carrying the SARS-CoV-2.

With regard to current testing protocols for SARS-CoV-2, however, a single positive test result for SARS-CoV-2 is only accurate in the range of 75-90% without a pre-test evaluation, given the assumed range of prevalence (2-5%), sensitivity (80-85%), and specificity (99.5%). Further, Coronavirus Disease 2019 (COVID-19) only causes symptoms in about half of infected individuals, with the exception of at least a mild fever in about 90% of infected individuals. By measuring the temperature of individuals as part of the pre-test evaluation, however, the precision of the test can improve in the range of about 98.5-99.5% for feverish individuals, assuming 30-50% of fevers in the targeted population are caused by the disease. As such, through the accurate identification of the presence of a fever in a user, the precision of the test can be greatly improved. Due to a user's natural diurnal curve and other characteristics contained within a temperature dataset, accurately identifying a fever in a particular user can be challenging.

The temperature sensing probe 102 in accordance with the present disclosure, along with the diurnal curve analytics described herein, can be utilized to beneficially provide useful body temperature insights that can be used to in pre-test evaluations. More particularly, adjustments to the pre-test probability of various medical testing procedures, such as a real-time reverse transcription polymerase chain reaction test (PCR Test), can be made based on the temperature insights. As provided above, a diurnal curve for a particular user that is being testing can be generated based on the user's actual temperature data collected over time (i.e., their baseline diurnal curve) and/or based on diurnal curve modeling (i.e., based on the user's gender and age, for example).

In accordance with some forms of testing, for example, the presence of a fever event can be defined as a 1.5° C. increase in body temperature. Using a diurnal curve applicable to that particular user, a more precise determination of a fever event can be provided in accordance with the system and methods provided herein. That determination can then be used in the pre-test evaluation of the user. For example, the presence or absence of a fever can be used to adjust the pre-test probability of a PCR Test and/or other type of medical diagnostic test. Accordingly, diurnal curve based fever determination in accordance with the present disclosure can be useful as a pre-screening tool in targeting and/or prioritizing the testing of individuals for SARS-CoV-2. Additionally, using real-time fever data analyzed on a macro scale, as collected in accordance with the present disclosure, testing for SARS-CoV-2 in certain geographic areas can be prioritized over other areas, in the interest of efficiently and rapidly identifying infected individuals. For instance, by selectively targeting geographic areas in the early stages of an outbreak, transmission rates can be reduced in a cost-efficient manner.

Figure 14:
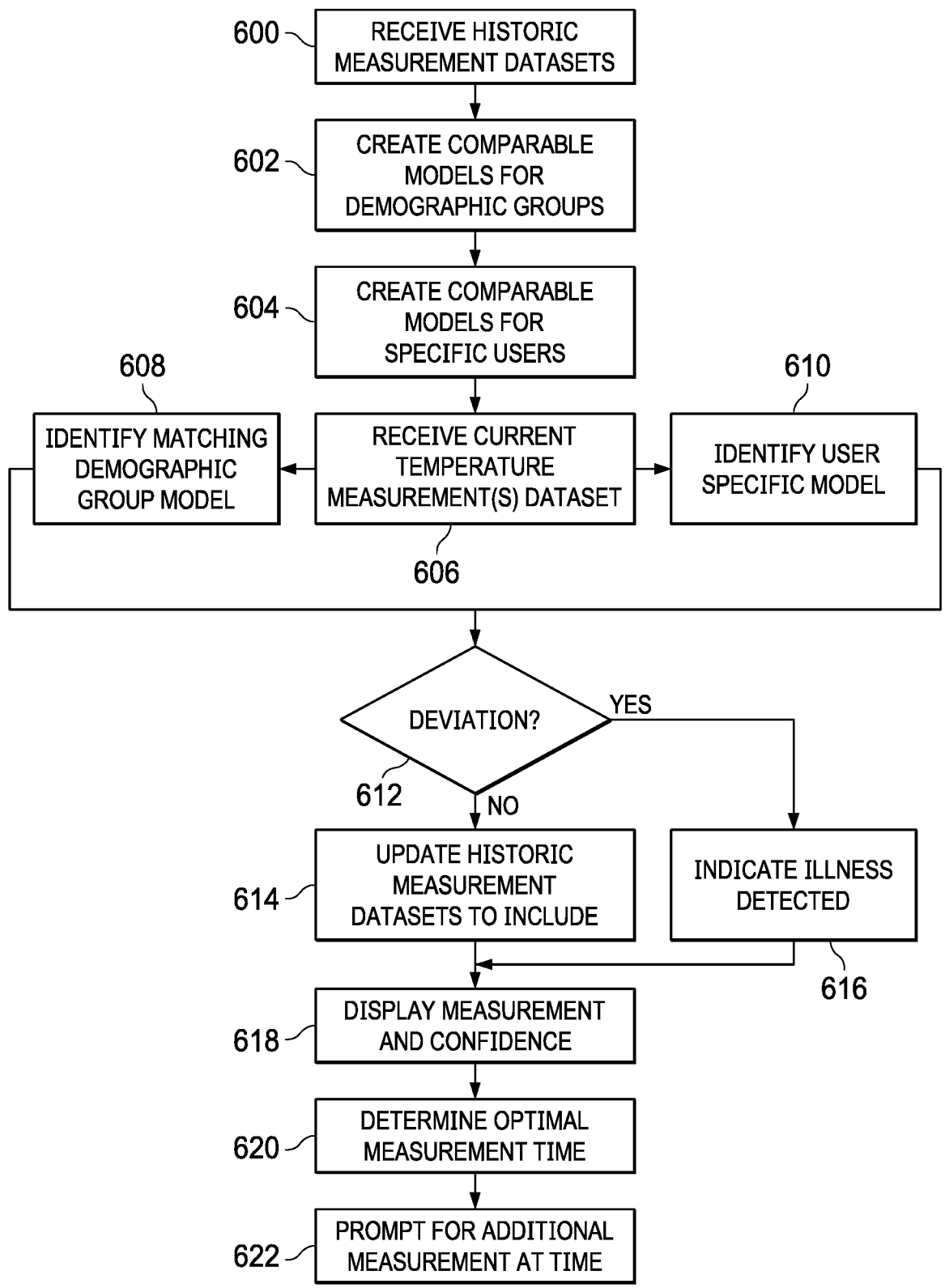
FIG. 14 is a flowchart of an exemplary set of steps that may be performed to detect febrile illness.

FIG. 14 shows an exemplary set of steps that may be performed by a system such as that illustrated in FIGS. 1, 12 and 13, or a variation thereof, in order to detect febrile illness using temperature datasets created from specific demographic group data or from specific user data. The steps of FIG. 14 may be performed by a single device or across a combinations of devices (e.g., the thermometer 102, auxiliary user device 104, cloud server 108, and data infrastructure 118).

The system may receive 600 historic temperature measurement datasets that describe temperature measurements for a plurality of individuals over time. These datasets may include some or all of temperature measurements, times at which temperature measurements are taken, demographic information about the source individual for the temperature measurements (e.g., age, gender, location, physiological condition as measured by a sensor, physiological condition as selected by the individual, etc.), and unique identifying information for the individual (e.g., an email address, user name, or user identifier number that is uniquely assigned within the system). Datasets may be received from individual users of the system when the system is interacted with (e.g., a user's current temperature measurement may subsequently be added to an aggregate of historic datasets), or may be received by the system as aggregate data produced by trials or studies, for example.

The system may create 602 a plurality of comparable models for different demographic groups based on the historic measurement datasets. As an example, these comparable models may be a combination of a data structure that organizes relevant data from the historic datasets into a structured format, as well as functions or methods that allow for comparison between such data structures, or comparison to individual data points associated with such structures. As an example, one such structure might be a data structure representing a diurnal curve for a specific demographic group with ranges of observed temperatures over a 24 hour period. Such a structure might include or be associated with functions or methods that may be invoked to compare that structure to another similar structure and note any substantial differences or deviations between the two, or to compare one or a small number of data points to that structure to determine if individual data points fall outside of an expected range relative to that structure. Multiple demographic group models may be created from the same historic measurement datasets, and may cover singular demographic features (e.g., age) or combinations of demographic features (e.g., age+gender, age+gender+ethnicity) or other characteristics of the individual or the circumstances in which measurements were produced (e.g., geographical location, ambient temperature at capture time, heart rate at capture time, high physical activity prior to capture time).

The system may create 604 a plurality of comparable models for specific users of the system, in addition to or as an alternative to creating 602 comparable models for specific demographic groups. User specific models may function similarly to the comparable models created 602 for demographic groups, but may be created from historic measurement datasets associated with a particular user rather than sourced from an entire demographic group. As an example, when initially using the system, a user's temperature measurements may be analyzed using demographic group models for groups similar to the user. As the system is populated with measurements taken from that user over a period of days or months, the user's temperature measurements may be analyzed against their own user specific models instead of or in addition to other analyses.

The system may then receive 606 a current temperature measurement, or a set of temperature measurements, for a particular user. Current measurement datasets may include temperature measurements, as well as information identifying the user (e.g., a user identifier unique to the system) or identifying a demographic group of the user (e.g., an indication of the user's age and gender), and in some implementations may also include additional data describing the user or the circumstances of the measurement (e.g., geographical location, ambient temperature, etc.).

The system may identify 608 a demographic group model that matches that of the user, which may include identifying 608 a model having identical demographic features, or a model having substantially the same demographic features (e.g., a 65 year old user may be matched to a model created from temperature measurements of 60-70 year old sources). The system may analyze the current measurement dataset using the identified 608 model and determine if the current measurement dataset presents any deviations 612 from that expressed by the identified 608 model. This may include creating a data structure or other model of the current measurement dataset where it contains multiple temperature measurements over a period of time, and then performing a model to model analysis, or may include comparing one or several individual measurements to the identified 608 model (e.g., comparing a current measurement captured at 9:15 am to a portion of the model associated with historic measurements captured between 9:00 am and 9:30 am). A deviation 612 may exist based on one or several factors, as has been described above, which may include evaluation of configured thresholds, ranges, magnitudes of deviation, abnormal curves, plots, lines, or other aspects of the model.

The system may identify 610 a user specific model in addition to or in the alternative to identifying 608 a demographic group model. User specific models may be available for users that have provided sufficient temperature measurements to the system, and may be identified based on matching certain unique user information (e.g., a user identifier, username, email address, etc.) provided by the user with the same information that is stored and associated with the user specific model. Evaluation of the current measurements against the identified 610 user specific model may occur as described above in the context of the demographic group model, and may include model to model comparisons for multiple data points or evaluation of one or several data points to identify any deviations 612 from the expected temperature measurements or models.

Where no deviation 612 exists, the system may update 614 the historic measurement datasets to include the current measurements, which may include updating one or more demographic group models, user specific models, or both to account for the newly captured data points. Where a deviation 612 is identified, the system may provide an indication 616 that a febrile illness has been detected based on the current measurement dataset, which may include providing an audible or visible alarm (e.g., via the thermometer 102 or auxiliary user device 104), providing an electronic message to one or more recipients (e.g., auxiliary user devices 104 in the possession of a patient or care provider), or providing software application notifications via the user application 116 or other software application executing on one or more devices.

The system may also display 618 the current temperature measurement and any related data, and may also determine and display a confidence rating associated with that temperature measurement. The confidence rating may be based upon factors such as the current temperature measurement, the determination as to whether it deviates 612 from comparable models and to what extent, the user's demographic information, the time of day at which the measurement is captured, and upon the historic measurement datasets and/or the comparable models themselves. As an example, with reference to FIG. 11, a measurement from a 65 year old user taken around 10:00 am may be determined to have a low confidence rating unless the measurement deviates 612 so greatly from the expected range that it is very likely to indicate a febrile illness (or lack thereof) despite the low probability of observing fever at that time. Similarly, a measurement taken from a 65 year old user around 8:00 pm may be determined to have a high rating based on the probability of observing fever at that time, with such confidence rating be further influenced by the magnitude of any deviation 612 that is present. The measurement and/or confidence rating may be displayed via one or more of the described devices such as the thermometer 102, the auxiliary user device 104, or a device executing the user application 116, and may be displayed via a user interface having text, numerals, visual indicators representing confidence (e.g., shapes, colors, symbols, or other visual indicators), or other visual characteristics.

In some implementations, the system may also determine 620 an optimal measurement time for the user based on their demographic information, recent temperature measurements, confidence scores in recent temperature measurements, and other information. As an example, where a 65 year old user measures their temperature at 10:00 am and receives a low confidence score for confirming whether or not a febrile illness exists, the system may automatically determine 620 (e.g., based on historical measurement datasets, demographic models, or user specific models) that an ideal time for measurement may be 8:00 pm, or may be a four hour period between 6:00 pm and 10:00 pm with measurements taken every fifteen minutes. Based on this, the system may then prompt 622 the user (e.g., via the auxiliary user device 104 or another device in their possession or the possession of a care provider) to capture additional temperature measurements at the determined 620 time or times, with such additional measurements being evaluated using steps such as those described in order to provide an indication of febrile illness with a high confidence rating.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art.

What is claimed is:

1. An illness detection and tracking system, comprising:
a temperature sensing probe configured to produce user temperature measurements associated with a user;
a display that is configured to be held or worn by the user;
one or more storage devices configured to store one or more temperature datasets, wherein each of the one or more temperature datasets:
includes a set of temperature measurements that are each associated with a measurement time;
is associated with one or more source characteristics that describe a source of the set of temperature measurements;
one or more processors in communication with the temperature sensing probe, wherein the one or more processors are configured to:
receive a set of user characteristics that describe the user;
identify a matching temperature dataset of the one or more temperature datasets based on a comparison of the set of user characteristics to the one or more source characteristics;
receive a current user temperature measurement from the temperature sensing probe;
determine a capture time at which the current user temperature measurement was produced by the temperature sensing probe;
compare the current user temperature measurement to the matching temperature dataset based on the capture time to determine whether the current user temperature measurement falls outside of a configured threshold of an expected user temperature measurement at the capture time;
and in response to determining whether the current user temperature measurement falls outside of the configured threshold, determine a confidence rating that describes a likelihood that the user is suffering from a febrile illness based on the capture time and the comparison of the current user temperature measurement to the matching temperature dataset;
and cause the display to show:
an indication of whether the current user temperature measurement falls outside of the configured threshold of the expected user temperature measurement, wherein the indication comprises the current user temperature measurement;
and the confidence rating that describes the likelihood that the user is suffering from a febrile illness.

2. The system of claim 1, wherein the one or more processors are further configured to:
receive a plurality of current user temperature measurements from the temperature sensing probe over a period of time;
determine capture times for each of the plurality of current user temperature measurements;
create a measured temperature model that describes the plurality of current user temperature measurements and their capture times over the period of time;
create a comparison temperature model that describes the matching temperature dataset;
when comparing the current user temperature measurement to the matching temperature dataset, compare the measured temperature model to the comparison temperature model at the same period of time to determine if the measured temperature model deviates from the comparison temperature model beyond the configured threshold over that period of time.

3. The system of claim 1, wherein each of the one or more temperature datasets:
is associated with a combination of age and gender; and
includes temperature measurements taken from a plurality of individuals having said combination of age and gender.

4. The illness detection and tracking computing system of claim 1, wherein determining whether the real-time user temperature reading deviates from the identified baseline diurnal curve comprises determining whether the real-time user temperature reading exceeds a threshold value.

5. The illness detection and tracking computing system of claim 4, wherein the threshold value is dependent on a time of day of the real-time user temperature reading.

6. The illness detection and tracking computing system of claim 4, wherein the threshold value is dependent on a demographic of the respective user associated with the real-time user temperature reading.

7. An illness detection and tracking computing system, comprising:
a plurality of temperature sensing probes, wherein each of the temperature sensing probes is configured to communicate with an associated user device, the user device comprising a processor and a display;
a centralized illness detection and tracking computing system comprising at least one memory and at least one processor, wherein the illness detection and tracking computing system is in networked communication with each of the associated user devices, wherein the at least one memory stores instructions which when executed cause the illness detection and tracking computing system to:

over a period of time receive sets of user data from each of the user devices via network communications, wherein each set of user data received from each of the computing user devices comprises a user temperature reading as collected by an associated temperature sensing probe of the plurality of temperature sensing probes and a time stamp associated with each of the user temperature readings, wherein each set of user data is associated with a respective user;

generate and store a plurality of baseline diurnal curves, wherein each of the plurality of baseline diurnal curves is associated with the respective user and is generated based on the sets of user data received over the period of time for the respective user; receive a real-time user temperature reading and a capture time associated with the real-time temperature reading from the user device of one of the respective users;

identify a baseline diurnal curve from the plurality of baseline diurnal curves that is associated with said respective user;

based on the real-time user temperature reading and the capture time, compare the real-time user temperature reading to the identified baseline diurnal curve and determine whether the real-time user temperature reading deviates from the identified baseline diurnal curve;

based on the comparison of the real-time user temperature reading to the identified baseline diurnal curve and the capture time, determine a confidence rating that describes a likelihood that the user is suffering from a febrile illness;

and cause the display of the user device of said respective user to show:

an indication of whether the real-time user temperature reading deviates from the identified baseline diurnal curve, wherein the indication comprises the real-time user temperature reading;

and the confidence rating that describes the likelihood that the user is suffering from a febrile illness.

8. The illness detection and tracking computing system of claim 7, wherein the instructions further cause the illness detection and tracking computing system to:

provide the indication and the confidence rating to a third party user device.

9. The illness detection and tracking computing system of claim 7, wherein the period of time is at least a 48 hour period.

10. The illness detection and tracking computing system of claim 7, wherein at least three temperature readings are collected every 24 hours during the period of time.

11. The illness detection and tracking computing system of claim 7, wherein the temperature readings are continually collected over the period of time.

12. The illness detection and tracking and system of claim 7, wherein the temperature sensing probe is a medical thermometer.

13. The illness detection and tracking and system of claim 7, wherein the temperature sensing probe is a wearable fitness tracker.

14. The illness detection and tracking computing system of claim 7, wherein each of the user devices is any of a smart phone, a tablet computer, a laptop computer, and a desktop computer.

15. An illness detection and tracking computing system, comprising:

a plurality of temperature sensing probes, wherein each of the temperature sensing probes is configured to communicate with an associated user device, the user device comprising a processor and a display;

a centralized illness detection and tracking computing system comprising at least one memory and at least one processor, wherein the illness detection and tracking computing system is in networked communication with each of the associated user devices, wherein the at least one memory stores instructions which when executed cause the illness detection and tracking computing system to:

store a plurality of diurnal curve probability models in a data store, wherein each of the plurality of diurnal curve probability models is associated with a respective user demographic;

receive user data from one of the user devices, wherein the user data comprises a time-stamped user temperature reading collected from a user by one of the of plurality of temperature sensing probes;

receive user demographic data from the user, wherein the user demographic data comprises an age of the user and a gender of the user;

based on the user demographic data, determine an applicable diurnal curve probability model from the plurality of diurnal curve probability models;

using the applicable diurnal curve probability model and the time-stamped user temperature reading, determine a probability of observing a fever of the user;

compare the time-stamped user temperature reading to the applicable baseline diurnal curve and determine whether the time-stamped user temperature reading deviates from the applicable baseline diurnal curve;

cause the display of said user device to show:

an indication of whether the time-stamped user temperature reading deviates from the applicable baseline diurnal curve, wherein the indication comprises the time-stamped user temperature reading; and the determined probability of observing a fever of the user.

16. The illness detection and tracking computing system of claim 15, wherein the instructions further cause the illness detection and tracking computing system to:

provide to a third party user device an indication of the probability of observing a fever of the user.

17. The illness detection and tracking and system of claim 15, wherein the temperature sensing probe is a medical thermometer.

18. The illness detection and tracking and system of claim 15, wherein the temperature sensing probe is a wearable fitness tracker.

19. The illness detection and tracking computing system of claim 15, wherein each of the user devices is any of a smart phone, a tablet computer, a laptop computer, and a desktop computer.

20. The illness detection and tracking computing system of claim 15, wherein the plurality of diurnal curve probability models comprises diurnal curve probability models segmented by age.

21. The illness detection and tracking computing system of claim 15, wherein the plurality of diurnal curve probability models comprises diurnal curve probability models segmented by gender.

22. The illness detection and tracking computing system of claim 15, wherein the plurality of diurnal curve probability models comprises diurnal curve probability models segmented by age and gender.

* * * * *